United States Patent
Kundalgurki

(10) Patent No.: US 9,658,180 B2
(45) Date of Patent: May 23, 2017

(54) SYSTEMS AND METHODS FOR DETECTING CHANGE IN SPECIES IN AN ENVIRONMENT

(71) Applicant: FREESCALE SEMICONDUCTOR, INC., Austin, TX (US)

(72) Inventor: Srivatsa G. Kundalgurki, Austin, TX (US)

(73) Assignee: NXP USA, Inc., Austin, TX (US)

( * ) Notice: Subject to any disclaimer, the term of this patent is extended or adjusted under 35 U.S.C. 154(b) by 0 days.

(21) Appl. No.: 14/625,008

(22) Filed: Feb. 18, 2015

(65) Prior Publication Data
US 2016/0238551 A1 Aug. 18, 2016

(51) Int. Cl.
| | |
|---|---|
| G01N 25/08 | (2006.01) |
| G01N 27/22 | (2006.01) |
| G01N 27/403 | (2006.01) |
| H01L 31/115 | (2006.01) |
| H01L 31/0224 | (2006.01) |
| G01N 33/00 | (2006.01) |

(52) U.S. Cl.
CPC ......... *G01N 27/226* (2013.01); *G01N 27/227* (2013.01); *G01N 27/228* (2013.01); *G01N 27/403* (2013.01); *G01N 33/0036* (2013.01); *H01L 31/022408* (2013.01); *H01L 31/115* (2013.01)

(58) Field of Classification Search
None
See application file for complete search history.

(56) References Cited

U.S. PATENT DOCUMENTS

| | | |
|---|---|---|
| 5,217,595 A | 6/1993 | Smith et al. |
| 7,414,245 B2 | 8/2008 | Trissel |
| 7,855,780 B1 | 12/2010 | Djeu |
| 8,492,722 B2 | 7/2013 | Chang et al. |
| 8,569,703 B2 | 10/2013 | Yu et al. |
| 2011/0204323 A1 | 8/2011 | Espiau De Lamaestre et al. |
| 2016/0071997 A1 | 3/2016 | Kundalgurki |

OTHER PUBLICATIONS

Greenshields, M.W.C.C. et al., AC-Conductance and Capacitance Measurements for Ethanol Vapor Detection Using Carbon Nanotube-Polyvinyl Alcohol Composite Based Devices, 2011, Journal of Nanoscience and Nanotechnology, vol. 11, pp. 2384-2388.*
Sohrabi et al, "A novel technique for rapid vapor detection using swelling polymer covered microstrip ring resonator", IEEE MTT-S International Microwave Symposium (IMS), Jun. 1-6, 2014, pp. 1-4, Tampa, FL.

(Continued)

*Primary Examiner* — Robert Xu

(57) ABSTRACT

The present disclosure provides embodiments for diodes, devices, and methods for polar vapor sensing. One embodiment of a diode includes a first electrode to which an electric field is applied; a second electrode to which the electric field is applied; and a vapor gap region between the first electrode and the second electrode. A total capacitance measured between the first electrode and the second electrode varies based on presence of a polar vapor species on at least a portion of an electrode surface of at least one of the first electrode and the second electrode.

13 Claims, 12 Drawing Sheets

(56) References Cited

OTHER PUBLICATIONS

Shishiyanu et al, "Novel Zinc Oxide Nanostructured thin Films for Volatile Organic Compaunds Gas Sensors", International Semiconductor Conference, Sep. 27-29, 2006, pp. 201-204, vol. 1, Sinaia.

Kanda et al, "Development of VOC analyzer using a WO3 thick film based gas sensor", Proceedings of IEEE Sensors, Oct. 24-27, 2004, pp. 1187-1190, vol. 3.

Elmi et al, "Ultra Low Power Mox Sensors with ppb-Level VOC Detection Capabilities", IEEE Sensors, Oct. 28-31, 2007, pp. 170-173, Atlanta, GA.

Dong et al, "Design of the photo-ionization detector of total hydrocarbon", International Conference on Optoelectronics and Microelectronics (ICOM), Sep. 7-9, 2013, pp. 98-100, IEEE, Harbin.

Ahmadi et al, "Theoretical Calculation of Radiation Induced Conductivity in Nanomaterials", IEEE International Conference on Nanotechnology, Aug. 15-18, 2011, pp. 1737-1740, Portland, OR.

Office Action—Restriction/Election for U.S. Appl. No. 14/476,957, mailed May 5, 2016, 6 pages.

Notice of Allowance, U.S. Appl. No. 14/476,957, Jan. 13, 2017, 12 pages.

Office Action for U.S. Appl. No. 14/837,147, Jan. 5, 2017, 12 pages.

Office Action for U.S. Appl. No. 14/476,957, Oct. 17, 2016, 12 pages.

Notice of Allowance for U.S. Appl. No. 14/837,147, Apr. 13, 2017, 7 pages.

\* cited by examiner

DEVICE RESPONSIVITY VS X-RAY ACCELERATION VOLTAGE

SYSTEMS AND METHODS FOR DETECTING CHANGE IN SPECIES IN AN ENVIRONMENT

FIELD OF THE INVENTION

The disclosure relates generally to semiconductor processes and devices, and more particularly to methods for forming semiconductor devices capable of detecting changes in species in vapor or particle form in an environment.

BACKGROUND OF THE INVENTION

There has been significant interest and research in the field of solid state photoelectric and biochemical vapor and particle detectors. In detecting various species in vapor and particle form, various relatively complex and high cost solutions have been developed, but are unsuitable for low cost, portable devices operating at room temperature.

A PIN diode is a semiconductor diode with a lightly doped intrinsic semiconductor region in a substrate between a p-type region and an n-type region. For particle detection, when radiation or charged particles of sufficient energy impact the intrinsic region, an electron-hole pair is created that generates current between the p-type and n-type regions. The p and n-type regions and the intrinsic region also have a measurable capacitance. The PIN diode can be used to detect photons as well as various types of charged particles including alpha particles and beta particles in a variety of sensors, such as radon sensors, radiation sensors, light sensors, and smoke detectors, among others.

One difficulty with using PIN diodes for sensors is the lack of sensitivity to detect indirectly ionizing neutrons because the impact of a neutron in the intrinsic region does not directly generate current as neutrons are electrically neutral. Additionally, the usefulness of a sensor is often proportional to the sensitivity of the PIN diode. It is therefore desirable to provide PIN diodes with enhanced levels of sensitivity, and with the ability to detect neutrons and to identify changes in vapor content in an environment, in addition to, or instead of, charged particles and photons.

BRIEF DESCRIPTION OF THE DRAWINGS

Embodiments of the present invention are illustrated by way of example and are not limited by the accompanying figures, in which like references indicate similar elements. Elements in the figures are illustrated for simplicity and clarity and have not necessarily been drawn to scale.

DETAILED DESCRIPTION

Embodiments disclosed herein provide an enhanced PIN diode detector with a silicon nanocluster-based scattering and electrically polarized primary interaction top layer (PIL) for vapor, photo particle, and/or ionization detection. When operating to detect a change in composition of a polar or charged vapor, the detector senses capacitance of electrodes to which the polar vapor has been attracted by a positive or negative charge on the electrodes. A change in the level of capacitance of the sensor system is an indicator of a change in the amount or composition of the vapor. Once a change in the capacitance is detected, this information may be provided to a controller so that appropriate action may be taken. For detecting photo particles or ionization, the nanoclusters are three-dimensional surfaces with high surface area encapsulated with dielectric that can be included in the sensor system to serve as physical scattering sites for incoming photon radiation. Compared to two-dimensional scattering sites, the increased surface area of the three-dimensional nanoclusters enhances absorption of the radiation in the underlying intrinsic region. Additionally, the interacting nanocluster dipoles in the enhanced PIN diode electric field induces deflection of charged particles such as alpha and beta particles in to the sensing volume, which further enhances the probability of detecting them. Still further, boron ($^{10}B$) isotope used as a nanocluster dopant generates ionizing alpha particles upon interaction with neutron radiation thereby enabling indirect detection of neutrons, which are otherwise hard to detect. The sensor system can be configured to detect changes in polar vapor and/or particles in an environment, and/or to detect charged and uncharged particles in the environment.

Figure 1:
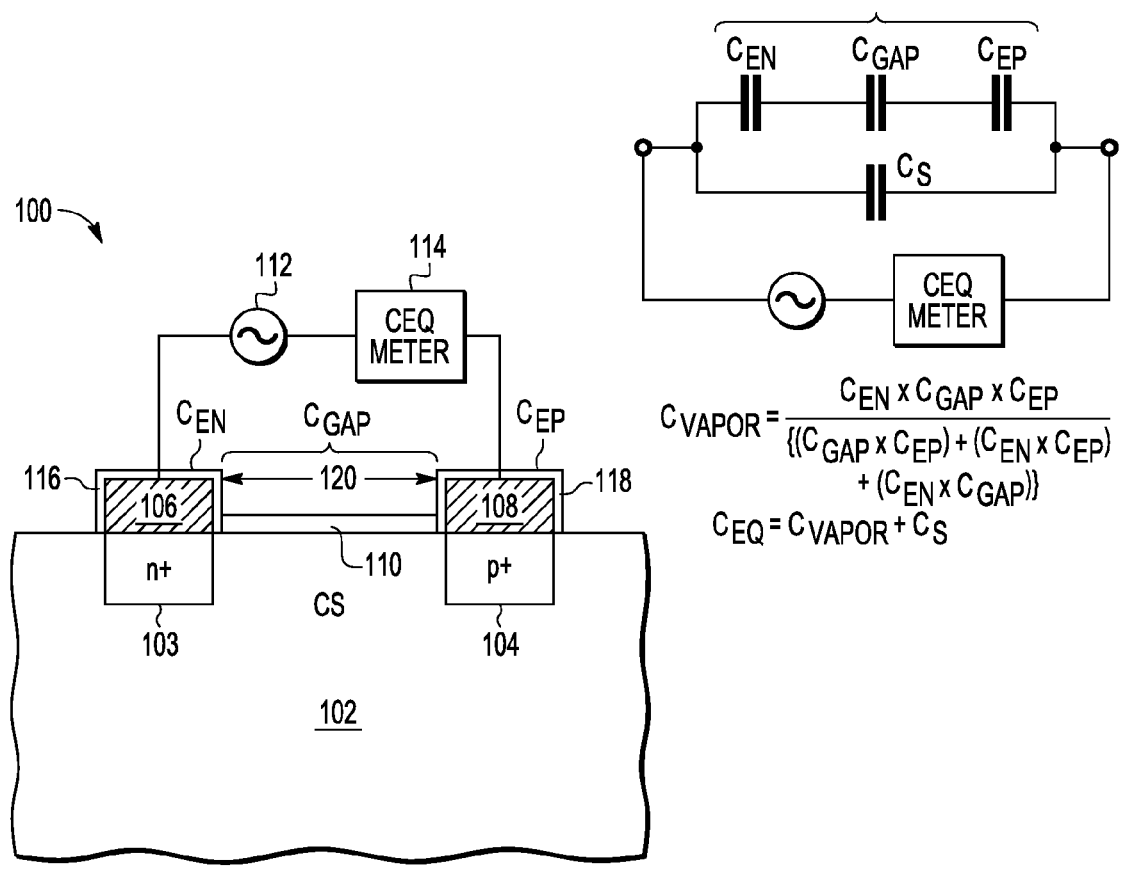
FIG. 1 is a block diagram of an embodiment of a vapor sensor system in accordance with the present invention.

FIG. 1 is a block diagram of an embodiment of a sensor system 100 in accordance with the present invention that includes semiconductor substrate 102, n-type doped region 103 and p-type doped region 104 in substrate 102, electrode 106 coupled in ohmic contact with n-type doped region 103, electrode 108 coupled in ohmic contact with p-type doped region 104, a layer of insulating material 110 grown or deposited on substrate 102 between electrodes 106 and 108, an alternating voltage source 112, and total or equivalent capacitance meter 114. Voltage source 112 and capacitance meter 114 are coupled in series with one another between electrode 106 and electrode 108. A first terminal of voltage source 112 is coupled to electrode 106, a second terminal of voltage source 112 is coupled to a first terminal of capacitance meter 114, and a second terminal of capacitance meter 114 is coupled to electrode 108. Insulating material 110 can be any suitable oxide or dielectric material that electrically insulates electrode 106 from electrode 108. Electrodes 106, 108 may be formed on substrate 102 by patterned etching a layer of aluminum or other electrically conductive material or other suitable technique for forming electrodes 106, 108. N-type doped region 103 may be implanted with phosphorous or other suitable material to have a higher concentration of electrons than substrate 102 and p-type doped region 104. P-type doped region 104 may be implanted with boron or other suitable material to have a higher concentration of holes than substrate 102 and n-type doped region 103. Sensor system 100 can operate at room temperature, but is also capable of operating at other ambient temperatures.

When alternating voltage is applied, an electric field around electrodes 106, 108 attracts charged vapor species that are capable of moving through the ambient environment in the proximity of electrodes 106, 108. For example, a polar molecule like water will have its positively charged hydrogen atoms attracted to and oriented towards a negative electrode and negatively charged oxygen atom oriented away from the negative electrode. An alternating voltage being applied between the two electrodes, 106, 108 will cause the water molecules to rotate in response to the changing electrode polarities at each of the two electrodes, 106, 108. This polarization phenomenon manifests itself as an electrode capacitance change which in turn alters the overall equivalent circuit capacitance of sensor system 100 which can be measured by total or equivalent capacitance meter (CEQ Meter) 114.

CEQ meter 114 is a logic circuit configured to measure the total capacitance of sensor system 100 including capacitance of electrodes 106, 108 (shown as CEN and CEP, respectively), substrate 102 (shown as CS), and vapor gap 120 (shown as CGAP) between electrodes 106, 108. When power of a known current (I) and voltage (V) is applied by alternating voltage source 112, the total or equivalent capacitance (CEQ) of sensor system 100 can be determined over time (t) using the relationship CEQ=I(t)/(dV/dt). As the number of polar molecules adsorbed on electrodes 106, 108 changes, an electric double layer 116, 118 forms on electrodes 106, 108, causing a corresponding change in overall capacitance of sensor system 100 to be detected. Accordingly, sensor system 114 is able to detect when a change in the vapor composition or concentration of the ambient environment occurs. A signal indicating the capacitance of sensor system 100 from CEQ meter 114 can be provided to a controller or other logic circuit (not shown) so that any appropriate action may be taken.

Figure 2:
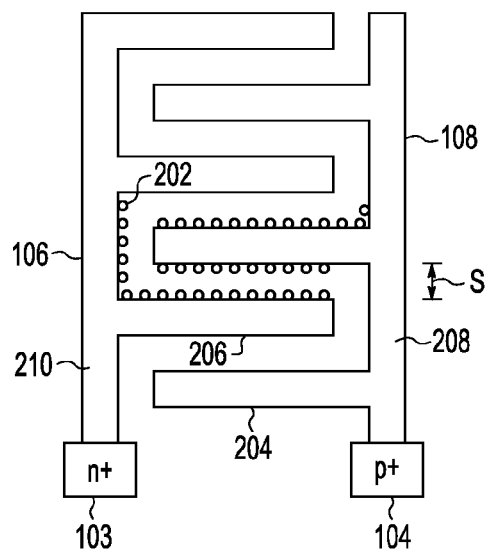
FIG. 2 is a top view of an embodiment of electrodes in the vapor sensor system of FIG. 1.

FIG. 2 is a top view of an embodiment of electrodes 106, 108 in the sensor system 100 of FIG. 1 in which electrodes 106, 108 each include a number of fingers 204, 206 alternatingly interlaced, or interdigitated, with one another. Any electrodes 106, 108 can include any suitable number of fingers 204, 206, for example, fifty or more fingers 204, 206 each. One end of each finger 204, 206 is attached perpendicular to a respective linear stem portion 208, 210. The other end of each finger 204, 206 extends toward but does not contact the stem portion 208, 210 of the other electrode 106, 108. The spacing (S) between fingers 204, 206 is selected to provide ample room for the vapor molecules or species 202 of interest to collect on the electrode 106, 108 to which the polar/charged molecule or specie is electrically attracted. The number of fingers 204, 206 can be chosen based on the amount of space available for sensor system 100 and the spacing S between fingers 204, 206. In one embodiment, fingers 204, 206 have a length of 1214 microns. The width of stem 208, 210 may vary based on spacing S. For example, width stem 208, 210 may vary from 454 microns at a spacing pitch of 0.5 microns to 804 microns at a spacing pitch of 4 microns. Other suitable values for spacing, length and width of fingers 204, 206, and stem, 208, 210 can be used.

Figure 3:
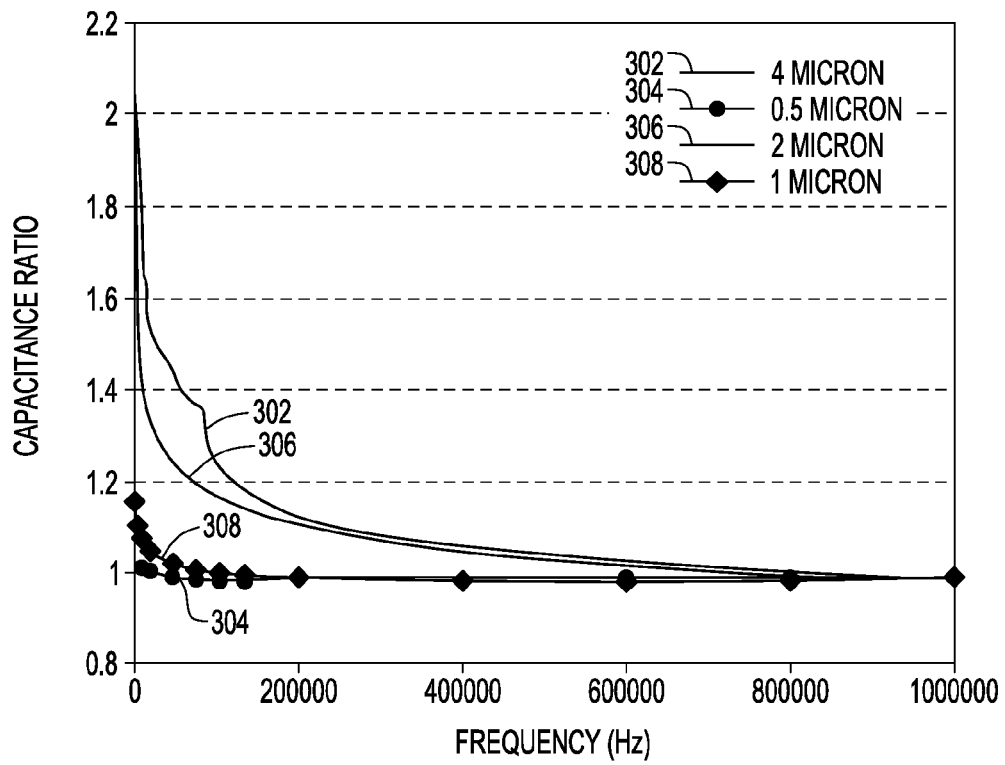
FIG. 3 is an example of a graph of capacitance ratio versus frequency at various spacings between the electrodes of FIG. 2.

FIG. 3 is an example of a graph 300 of capacitance ratio versus frequency at various spacing S between fingers 204, 206 of electrodes 106, 108 of FIG. 2. Capacitance ratio was derived by dividing the measured capacitance at any given frequency by its value at a capacitance of 1 MHz. At high frequencies approaching 1 MHz, the polar molecules of interest cannot rotate to keep up with the rapidly changing electric field and therefore the polarization capacitance contribution to the overall measured capacitance decreases and plateaus out to an electrode pitch independent constant low value. Therefore, the capacitance ratio can be used as a normalized value to quantify polarization effects as a function of electrode pitch. The tests for graph 300 were conducted in an ambient environment with the same concentration of vapor molecules. In graph 300, higher capacitance ratio indicates a greater number of vapor molecules collected on electrodes 106, 108 and/or enhanced polarization at lower frequencies. Four different values for spacing S were used, including 4, 2, 1 and 0.5 microns resulting in four respective traces 302, 306, 308, 304. Tests were conducted at frequencies of alternating voltage 112 (FIG. 1) ranging from 500 Hz to 1 MHz and an amplitude of 10 mV. The polar vapor species form an electric double layer at the surface of electrodes 106, 108 whose capacitance contribution to the overall equivalent capacitance increases inversely with measurement frequency and directly with vapor concentration. Accordingly, low frequency capacitance change can be correlated to a change in polar vapor concentration as the capacitance of the solid state PIN diode by itself is independent of measurement frequency and is unaffected by the vapor medium above it.

The highest capacitance for each trace 302, 304, 306, 308 occurs at the lowest frequency, or 500 Hz, with trace 302 at a normalized capacitance of above 2, trace 306 at a normalized capacitance just over 1.6, trace 308 at a normalized capacitance just under 1.2, and trace 304 at a normalized capacitance just over 1. Traces 302-308 decrease asymptotically from their highest values to a normalized capacitance of 1 at a frequency of 1 MHz. From graph 300, polarization of electrodes 106, 108 by the vapor molecules 202 in the environment increase equivalent capacitance of sensor system 100, with increasing capacitance at lower frequencies. Capacitance enhancement at lower frequencies seen at increasing finger widths is the result of the vapor molecules being able to more easily collect on electrodes 106, 108 at relaxed pitch conditions to affect electrode polarization behavior.

Figure 4:
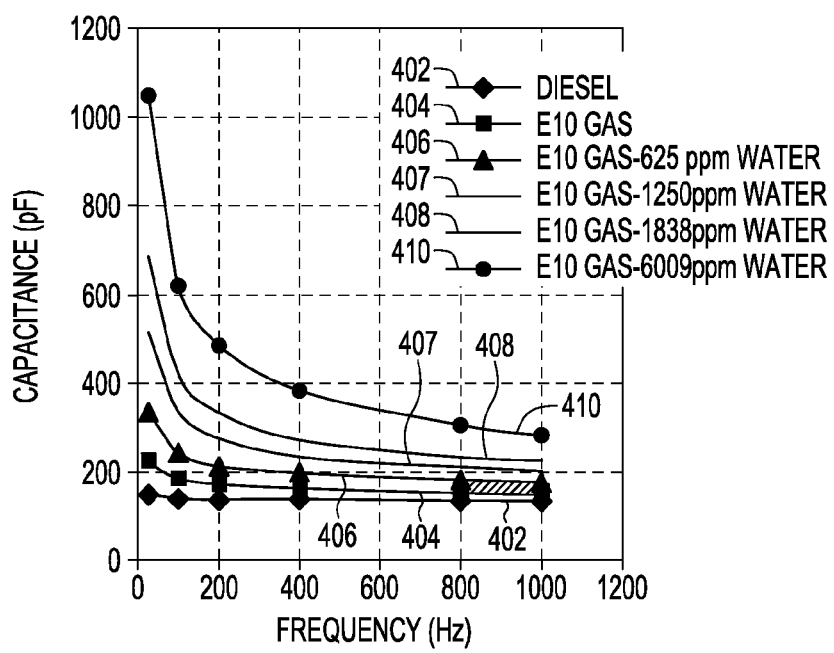
FIG. 4 is an example of a graph of capacitance versus frequency for water vapor detection for various water concentrations in a sample, as tested by the sensor system of FIG. 1.

FIG. 4 is an example of a graph 400 of capacitance versus frequency for water vapor detection for various water concentrations in a sample, as tested by sensor system 100 of FIG. 1. During the tests, a low frequency dielectric spectroscopic technique was used to discriminate between ethanol blended gasoline fuel and diesel fuel that included exploiting the difference in dielectric constant between the two fuels. Traces 402 and 404 show the capacitance in sensor system 100 over frequencies of alternating voltage 112 ranging from 30 Hz to 1 kHz. The equivalent capacitance of system 100 for diesel fuel as shown by trace 402 is approximately 153 picoFarads (pF) at 30 Hz. Trace 402 decreases asymptotically to a capacitance of approximately 134 pF at a frequency of 1 kHz. The equivalent capacitance of system 100 for ethanol blended gasoline fuel as shown by trace 404 is just above 223 picoFarads (pF) at 30 Hz. Trace 404 decreases asymptotically to a capacitance of approximately 146 pF at a frequency of 1 kHz. Adding ethanol to gasoline enables electrical discrimination between the two fuels since the dielectric constant of gasoline and diesel are about 2 while ethanol has a dielectric constant of 24.6 and water has a dielectric constant of 80.4.

Additionally, the same low frequency dielectric spectroscopic technique was used to quantify water contamination levels leading up to phase separation in a commercial ethanol-gasoline blend containing up to 10% ethanol. Traces 406, 407, 408, 410 show the capacitance in sensor system 100 over frequencies of alternating voltage 112 ranging from 30 Hz to 1 kHz for various combinations of water contamination in ethanol blended gasoline fuel. Generally, the higher the level of water contamination in the fuel blend, the higher the equivalent capacitance of sensor system 100. In the example shown in FIG. 4, the equivalent capacitance of system 100 for 625 (parts per million) water addition in ethanol blended gasoline fuel as shown by trace 406 is approximately 333 picoFarads (pF) at 30 Hz. Trace 406 decreases asymptotically to a capacitance of approximately 176 pF at a frequency of 1 kHz.

The equivalent capacitance of system 100 for 1250 (parts per million) water addition in ethanol blended gasoline fuel as shown by trace 407 is approximately 510 picoFarads (pF) at 30 Hz. Trace 407 decreases asymptotically to a capacitance of approximately 202 pF at a frequency of 1 kHz.

The equivalent capacitance of system 100 for 1838 (parts per million) water addition in ethanol blended gasoline fuel as shown by trace 408 is approximately 679 picoFarads (pF) at 30 Hz. Trace 408 decreases asymptotically to a capacitance of approximately 225 pF at a frequency of 1 kHz.

The equivalent capacitance of system 100 for 6009 (parts per million) water addition in ethanol blended gasoline fuel as shown by trace 410 is approximately 1050 picoFarads (pF) at 30 Hz. Trace 410 decreases asymptotically to a capacitance of approximately 284 pF at a frequency of 1 kHz.

Figure 5:
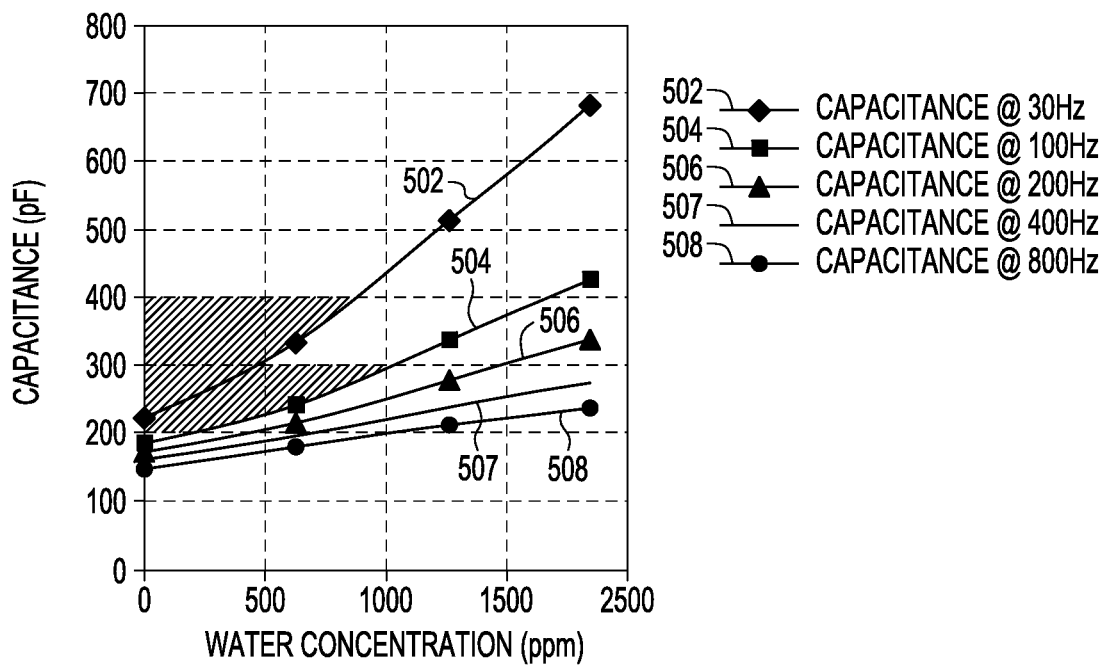
FIG. 5 shows an example of a graph of capacitance versus water concentration for water vapor detection at various frequencies, as tested by the sensor system of FIG. 1.

FIG. 5 is an example of a graph 500 of capacitance versus water concentration for water vapor detection at various frequencies, as tested by sensor system 100 of FIG. 1. Traces 502, 504, 506, 507, 508 show the capacitance in sensor system 100 over water additions ranging from 0 ppm to 1838 ppm in ethanol blended gasoline fuel at various frequencies. Generally, the lower the frequency of alternating voltage 112, the higher the equivalent capacitance of sensor system 100. In the example shown in FIG. 5, the equivalent capacitance of system 100 at a frequency of 30 Hz in ethanol blended gasoline fuel as shown by trace 502 increases from approximately 223 picoFarads (pF) at a water addition of 0 ppm to approximately 679 pF at a water concentration of 1838 ppm.

The equivalent capacitance of system 100 at a frequency of 100 Hz in ethanol blended gasoline fuel as shown by trace 504 increases from approximately 186 picoFarads (pF) at a water addition of 0 ppm to approximately 424 pF at a water concentration of 1838 ppm.

The equivalent capacitance of system 100 at a frequency of 200 Hz in ethanol blended gasoline fuel as shown by trace 506 increases from approximately 174 picoFarads (pF) at a water addition of 0 ppm to approximately 337 pF at a water concentration of 1838 ppm.

The equivalent capacitance of system 100 at a frequency of 400 Hz in ethanol blended gasoline fuel as shown by trace 507 increases from approximately 160 picoFarads (pF) at a water addition of 0 ppm to approximately 275 pF at a water concentration of 1838 ppm.

The equivalent capacitance of system 100 at a frequency of 800 Hz in ethanol blended gasoline fuel as shown by trace 508 increases from approximately 150 picoFarads (pF) at a water addition of 0 ppm to approximately 234 pF at a water concentration of 1838 ppm.

The ability to detect differences in fuel blends, as well as water contamination, could potentially be used both to achieve feed-forward control of a flex-fuel engine over a range of ethanol content levels as well as detecting above nominal water contamination levels in the fuel. If water contamination or improper fuel blend is detected, preemptive action could be taken before phase separation occurs. FIGS. 4 and 5 also highlight the point that equivalent capacitance of sensor system 100, and therefore detection rates, increase at lower alternating voltage frequencies.

Figure 6:
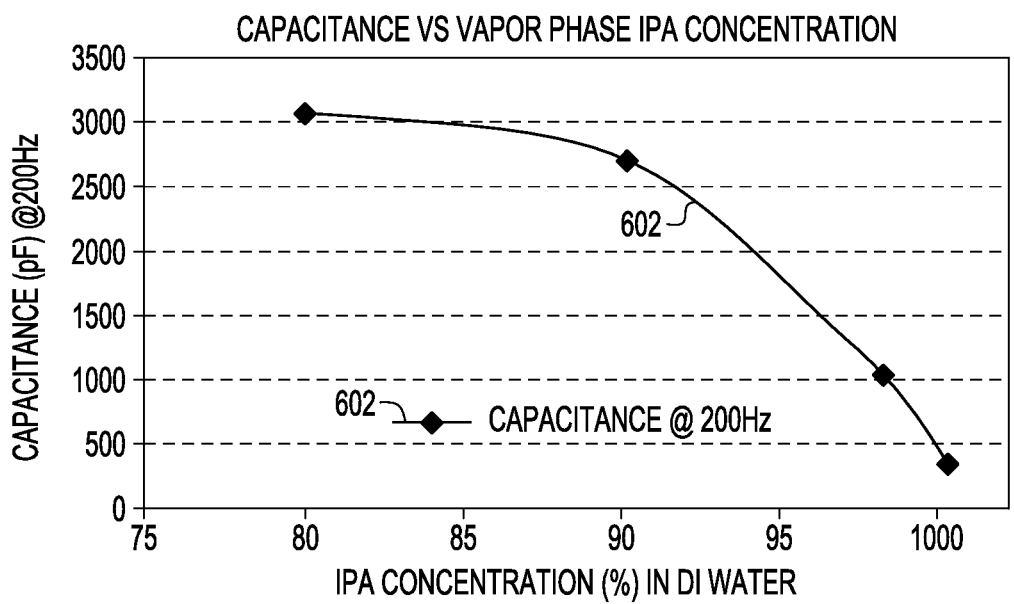
FIG. 6 is an example of a graph of capacitance versus alcohol concentration in water, as tested by the sensor system of FIG. 1 at a particular frequency.

FIG. 6 is an example of a graph 600 of capacitance versus alcohol concentration in water, as tested by the sensor system of FIG. 1 at a frequency of 200 Hz. Sensor system 100 has remarkable sensitivity to low levels of moisture in solvent vapor such as isopropyl alcohol (IPA), as quantified by its capacitance change versus water content in trace 602. The equivalent capacitance of system 100 at a frequency of 200 Hz as shown by trace 602 decreases from approximately 3081 pF at an IPA concentration of 80% to approximately 2707 pF at an IPA concentration of 90%, approximately 1035 pF at an IPA concentration of 98%, and approximately 362 pF at an IPA concentration of 100%. This behavior can be used to detect trace moisture contamination of solvents in storage before the solvent is used. In addition, sensor system 100 can be used to monitor IPA-based semiconductor end-point drying processes where the vapor-liquid equilibrium conforms to Raoult's law to insure the parts are completely dry, among other uses.

Figure 7:
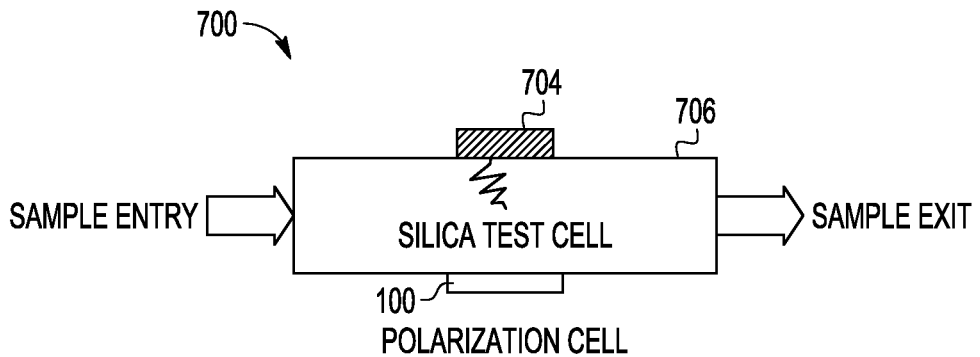
FIG. 7 is an embodiment of another sensor system that can be used to detect acetone even when mixed with ethanol.

Dielectric spectroscopic behavior of acetone and ethanol are quite similar. Therefore, sensor system 100 alone cannot be used to distinguish and negate the interfering effects of ethanol and humidity during sensitive acetone concentration measurements. Such a test may be encountered when analyzing the breath of a person with high blood glucose levels who is also suspected of being intoxicated with alcohol. The acetone present in the breath of a person with high blood sugar would interfere with detection of ethanol derived from consuming alcoholic beverages. To overcome the limitations of sensor system 100 in this situation, an embodiment of sensor system 700 is shown in FIG. 7 that can be used to detect acetone even when mixed with ethanol.

Sensor system 700 includes sensor system 100 in a housing or enclosure 706 and a selectively reactive source 704 of, for example, ultraviolet C (UVC) radiation 704 with a wavelength ranging from 280 to 100 nanometers. UVC radiation source 704 is oriented to transmit light to irradiate the vapor sample to be measured by sensor system 100. The ozone produced by the UVC radiation source 704 reacts with the acetone in housing 706, forming carbon dioxide, water and oxygen. Photochemical transitions of common interfering ethanol and water molecules occur at much lower UVC wavelengths so the selective oxidation of acetone using UVC radiation can be used to determine the polarization capacitance contribution from the acetone component and hence its original concentration in the vapor phase. Additionally, the double bond of the acetone carbonyl group is more reactive than the single bonds in ethanol, so purely from an ozone reactivity perspective, ozone is more reactive with acetone than with ethanol, also enabling chemical selectivity.

During operation, the capacitance of an initial breath sample can be measured without radiation from UVC radiation source 704 at low frequency of alternating voltage 112. UVC radiation source 704 is then activated and UVC light transmitted for a predetermined amount of time to oxidize the acetone in the sample. UVC radiation source 704 is then deactivated to terminate the acetone oxidation reaction. The capacitance of the oxidized breath sample is then measured at the same low frequency as the initial breath sample, without UVC radiation. At any given frequency, the difference in capacitance between the initial sample and the oxidized sample can be correlated to the original acetone concentration in the sample.

Note that alternative or more selectively reactive sources 704 can be used in sensor system 700 in addition to, or instead of, UVC radiation source, to enable sensor system 700 to discriminate between two or more different compounds in a vapor sample.

Figure 8:
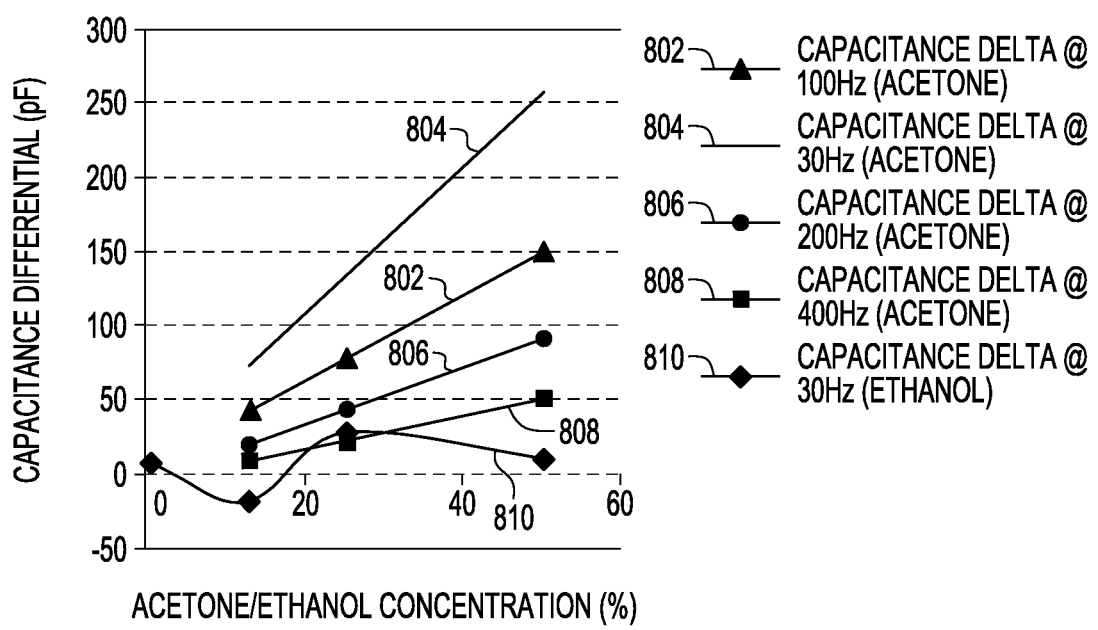
FIG. 8 is an example of a graph of capacitance versus acetone/ethanol concentration, as tested by the sensor system of FIG. 7 at various frequencies.

FIG. 8 is an example of a graph 800 of capacitance versus acetone/ethanol concentration, as tested by the sensor system of FIG. 7 at various frequencies. Traces 802, 804, 806, 808, 810 show examples of the difference in capacitance in sensor system 700 over acetone or ethanol concentrations ranging from 0 percent to 50 percent in water at various frequencies of alternating voltage 112. The differential capacitance of system 700 at a frequency of 100 Hz as shown by trace 802 increases linearly from approximately 42 picoFarads (pF) at an acetone concentration of 12.5 percent to approximately 152 pF at an acetone concentration of 50 percent.

The differential capacitance of system 700 at a frequency of 30 Hz as shown by trace 804 increases linearly from approximately 71 picoFarads (pF) at an acetone concentration of 12.5 percent to approximately 260 pF at an acetone concentration of 50 percent.

The differential capacitance of system 700 at a frequency of 200 Hz as shown by trace 806 increases linearly from approximately 20 picoFarads (pF) at an acetone concentration of 12.5 percent to approximately 94 pF at an acetone concentration of 50 percent.

The differential capacitance of system 700 at a frequency of 400 Hz as shown by trace 808 increases linearly from approximately 9 picoFarads (pF) at an acetone concentration of 12.5 percent to approximately 54 pF at an acetone concentration of 50 percent.

The differential capacitance of system 700 at a frequency of 30 Hz as shown by trace 810 is less than 30 pF for ethanol concentrations ranging from 0 to 50 percent.

Acetone has a dielectric constant of 20.7. Upon 3 minutes of ozone exposure, approximately 45% of the original volume of the acetone is lost to gaseous carbon dioxide and oxygen formation, both of which have a dielectric constant close to 1. This decomposition leads to a net reduction in the dielectric constant of the vapor phase in proportion to the original acetone concentration. In the tests represented by the results in graph 800, two capacitance measurements are taken, one of the initial vapor phase and second of the vapor after UV exposure. The difference between the two capacitance measurements is proportional to the original acetone content in the sample. The relationship between differential capacitance and acetone concentration is very linear. Also, an inverse relationship is exhibited between measurement sensitivity and alternating voltage frequency. The reactivity of ozone with ethanol under similar conditions however does not lead to a significant change in vapor phase dielectric constant and hence the observed selectivity. This is explained by (a) reduced volumetric loss of ethanol from 3 min ozone exposure of 15% relative to 45% for acetone, suggesting only partial oxidation to $CO_2$ per the reaction: $C_2H_5OH+4O_3 \rightarrow 2CO_2+3H_2O+3O_2$ and (b) preferential formation of acetaldehyde as the oxidation product with a dielectric constant close to the original ethanol per the reaction: $C_2H_5OH+O_3 \rightarrow CH_3CHO+H_2O+O_2$.

Figure 9:
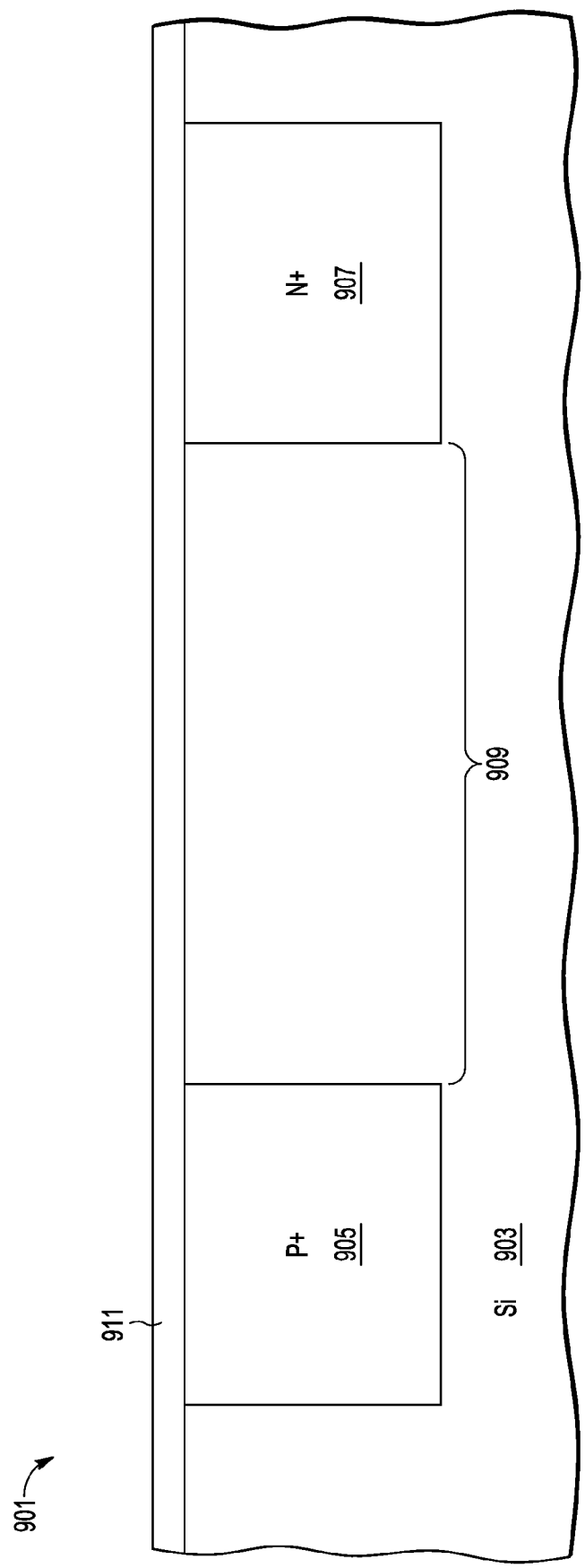
FIG. 9 is a cross-sectional side view of a portion of a PIN diode, at an intermediate stage of manufacture, according to an embodiment of the invention.

FIGS. 9-15 illustrate an example of a PIN diode 901 that can be used in sensor systems 100 and 700 to combine a polar vapor sensor with a radiation sensor. FIG. 9 is a cross-sectional side view of a portion of PIN diode 901 at an intermediate stage of manufacture, according to an embodiment of the invention that includes substrate 903 with p-type doped region (also referred to at P region) 905, n-type doped region (also referred to as N region) 907, intrinsic region 909, and insulating (also called oxide or dielectric) layer 911. P-type doped region 905 and n-type doped region 907 extend from a first major surface of substrate 903 to an intermediate level within substrate 903. For example, the p and n-type regions 905, 907 can be defined with boron and phosphorous dopants respectively via chain implantation to a depth of about 1 micron with a SIMS measured dopant concentration of about 2e18 atoms/cm$^3$. Intrinsic region 909 extends between and under regions 905 and 907.

The substrate 903 can be a semiconductor material or combination of materials such as, for example, polycrystalline silicon, monocrystalline silicon, amorphous silicon, gallium arsenide, silicon germanium, silicon-on-insulator (SOI), among other semiconductive material(s). For example, substrate 903 can be a 200 mm p-type silicon substrate with an intrinsic resistivity of 1000 ohm-cm.

Insulating layer 911 can be formed over substrate 903 using conventional growth or deposition processes. Insulating layer 911 can be, for example, $SiO_2$, HfAlO, $HfO_2$, ONO, SiON, SiN, or other dielectric or insulative material, including high dielectric constant material such as alumina, titanium dioxide, hafnium dioxide, tantalum dioxide, and the like. For example, insulating layer 911 can be a thin LPCVD thermal grown oxide layer with a thickness ranging from 30 to 100 Angstroms or other suitable thickness.

Figure 10:
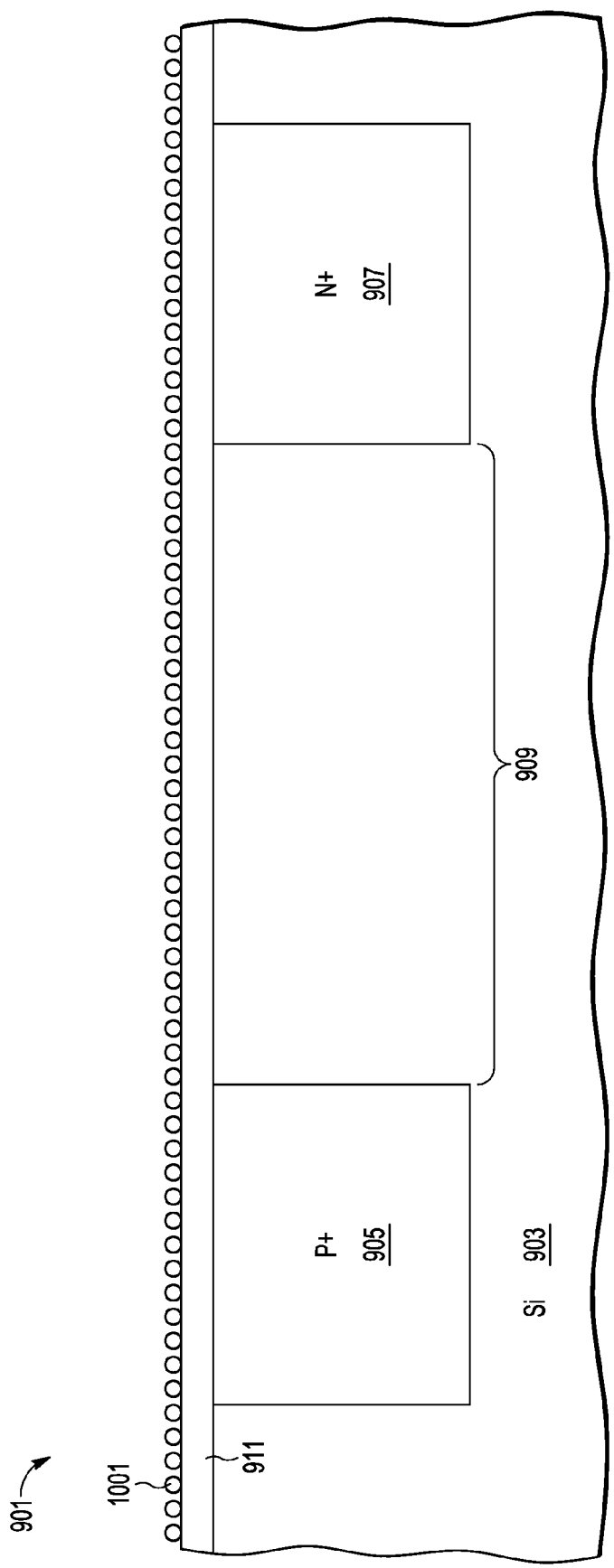
FIG. 10 is a cross-sectional side view of the PIN diode of FIG. 9, at a subsequent stage of manufacture, according to an embodiment of the invention.

FIG. 10 is a cross-sectional side view of the PIN diode of FIG. 9, at a subsequent stage of manufacture after a semiconductor layer 1001 is deposited over insulating layer 911. The deposition step can be performed using chemical vapor deposition (CVD), plasma enhanced chemical vapor deposition (PECVD), epitaxy (EPI) or other methods. In an embodiment, the substrate 903 can be placed in a deposition chamber and a precursor gas flowed into the chamber to form a thin non-contiguous semiconductor layer 1001 on the insulating layer 911. For example, an amorphous or a polysilicon layer 1001 can be formed by flowing a silicon precursor gas, such as silane ($SiH_4$) or disilane ($Si_2H_6$), for example, using a conventional CVD process. Deposition time will generally determine the thickness of the deposited layer 1001. In an embodiment, for example, the height or thickness of the semiconductor layer 1001 (e.g., amorphous/polycrystalline silicon) can be about 3-20 nm. In general, the deposition temperature is not so high as to control the thickness and morphology of the semiconductor (e.g., amorphous silicon) layer 1001.

Figure 11:
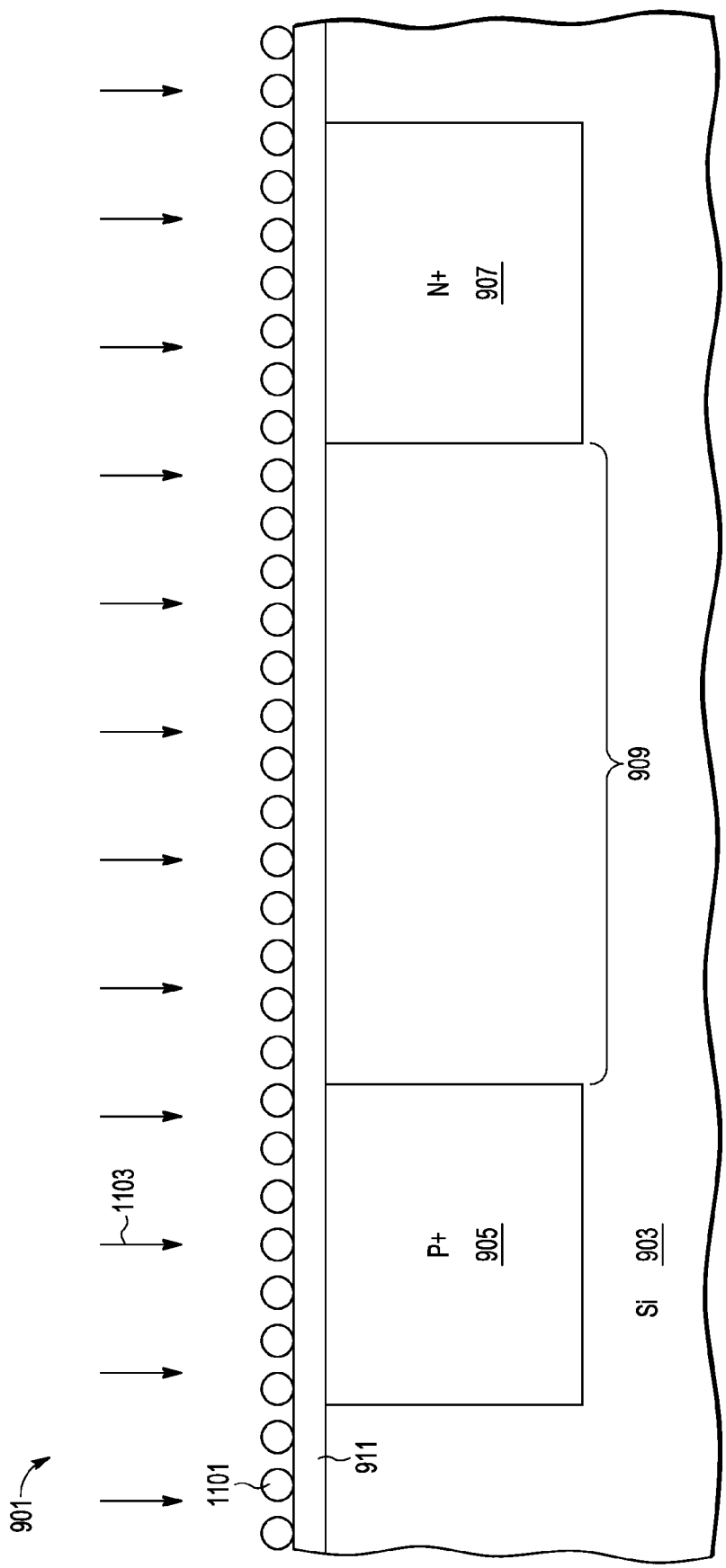
FIG. 11 is a cross-sectional side view of the PIN diode of FIG. 10, at a subsequent stage of manufacture, according to an embodiment of the invention.

FIG. 11 is a cross-sectional side view of the PIN diode of FIG. 10, at a subsequent stage of manufacture after which semiconductor layer 1001 (e.g., amorphous/polycrystalline silicon) is annealed to form nanoclusters 1101 of desirable shape and density. In an embodiment, the anneal 1103 of an amorphous/polysilicon layer 1001 can be performed in an ambient (e.g., one or more gases) that does not contain oxygen. For example, the ambient can be nitrogen, an inert gas (e.g., argon), hydrogen or a combination thereof. By way of example, an anneal 1103 of amorphous/polysilicon layer 1001 can be performed at a temperature of about 600-1000° C., for a time period of about 5-300 seconds in a hydrogen ambient.

Annealing the semiconductor layer 1001 results in the formation of a plurality of individual, discrete nanoclusters 1101 (also called nanoparticles) which are dispersed over the surface of the insulating layer 911. The anneal 1103 causes the semiconductor (e.g., amorphous/polysilicon) layer 1001 to dewet from the insulating layer 911 and form nanoclusters 1101 that are physically separated from each other. In some embodiments, for example, the nanoclusters 1101 can have an average diameter, thickness or height of about 10-30 nm and be separated or spaced from one another by 10-30 nm. Nanoclusters 1101 are generally uniformly distributed over the surface of the insulating layer 911, for example, at a density of about 1e11 to 3e11 nanoclusters per $cm^2$.

In some embodiments, for example, polysilicon nanoclusters 1101 can be LPCVD nucleated at 620 C followed by their coalescence and insitu doping with boron in an EPI reactor at 800 C. Boron doping can be accomplished through a diborane decomposition reaction which results in an approximately 20%-80% natural split co-doping of $^{10}B$ and $^{11}B$ isotope species.

Figure 12:
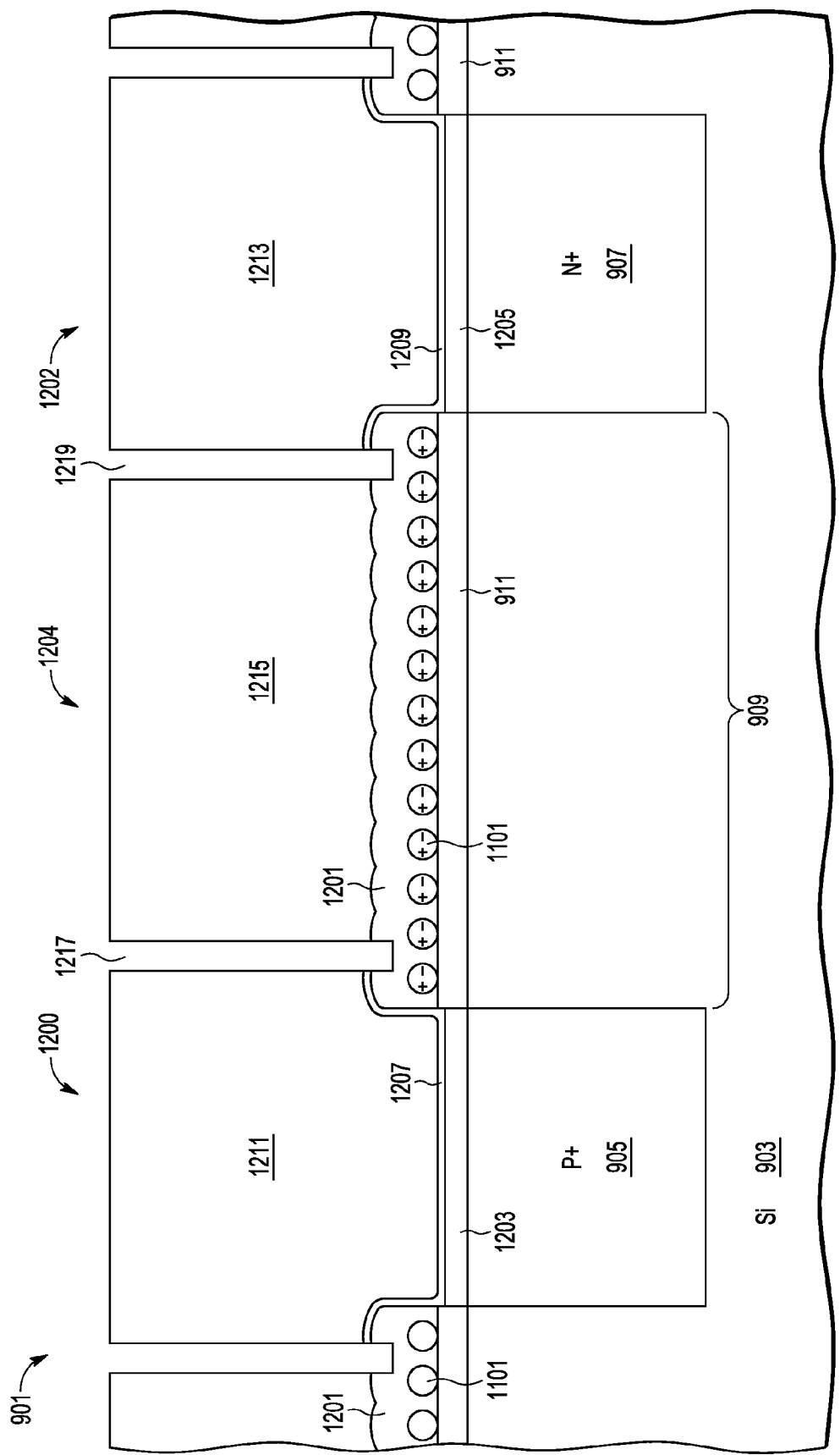
FIG. 12 is a cross-sectional side view of the PIN diode of FIG. 11, at a subsequent stage of manufacture, according to an embodiment of the invention.

FIG. 12 is a cross-sectional side view of the PIN diode of FIG. 11, at a subsequent stage of manufacture, according to an embodiment of the invention, after insulating layer (also referred to as dielectric or oxide layer) 1201 has been deposited over nanoclusters 1101 and a patterned etch has been performed on insulating layer 911, nanoclusters 1101 and insulating layer 1201 in a desired pattern that exposes the surface of substrate 903 in a first opening over p-type region 905 and in a second opening over n-type region 907. A conventional masking and etching process can be used to etch insulating layer 911, nanoclusters 1101 and insulating layer 1201. In some embodiments, the etching can be performed through a patterned mask such as a photoresist or other types of patternable material that can be selectively removed. The mask covers some of insulating layer 1201 and leaves desired areas for openings over regions 905, 907 exposed. The exposed areas over regions 905, 907 can then be etched, for example, by a conventional dry or wet etch process.

After the openings over regions 905, 907 are formed, a titanium silicide layer 1203, 1205 or other suitable material for improving ohmic contact with regions 905, 907 is formed selectively at the bottom of the respective openings. A layer of titanium nitride 1207, 1209 or other suitable barrier layer is then deposited over titanium silicide layers 1203, 1205, exposed sidewalls of the openings, and overlapping the top edge of insulating layer 1201 adjacent the openings. The titanium nitride layers 1207, 1209 or other material enables electrical contact to the regions 905, 907 while acting as a diffusion barrier between the underlying titanium silicide layers 1203, 1205 and metallization to be placed above titanium nitride layers 1207, 1209.

Electrodes (also referred to as ohmic contacts) 1211, 1213 are then formed in, above, and slightly overlapping the openings over regions 905, 907. Electrodes 1211, 1213 can be made of, for example, a patterned layer of aluminum, or other suitable conductive material. The thickness of electrodes 1211, 1213 is typically about 500 nm to several microns depending on the application. Electrodes 1211, 1213 can be patterned and etched by using conventional photolithographic processing (e.g., by dry etching) with a mask (not shown). The combination of electrode 1211, metallization layer 1207, silicide layer 1203 and p-type region 905 is referred to herein as p-terminal 1200 of PIN diode 901. The combination of electrode 1213, metallization layer 1209, silicide layer 1205, and n-type region 907 is referred to herein as n-terminal 1202 of PIN diode 901. The combination of insulating layers 1201, 911, nanoclusters 1101 and intrinsic region 909 is referred to herein as detection region 1204 of PIN diode 901.

In some embodiments, for example, nanoclusters 1101 can be encapsulated with a 100-200 nm plasma enhanced chemical vapor deposition undoped silicon glass (USG) cap layer, shown as insulative layer 1201, before being lithographically patterned to access the regions 905, 907 for subsequent contact formation. Once open, regions 905, 907 can be selectively silicided with titanium or titanium compound via RTP using a 12 second 685 C anneal resulting in titanium silicide formation. Subsequent metallization with titanium nitride metallization layers 1207, 1209 can include blanket deposition of a 250 A titanium nitride with 600 nm aluminum copper alloy (0.5% Cu) PVD stack. A chlorine-based endpointed reactive ion etch process can be used to pattern metallization layers 1207, 1209, 1211, 1213 with the etch tailored to reduce insulating layer 1201 to a thickness of 30-50 nm or lower in the open area from an original thickness ranging from 100-200 nm. Other suitable materials, processes, and thicknesses can be used in other embodiments.

In embodiments where optical isolation is desired, i.e., where detection of visible photons is not required, optical isolator 1215 can be added over intrinsic region 909 to block visible photons from reaching intrinsic region 909. Optical isolator 1215 can be made of any suitable opaque material, such as aluminum or other suitable material, with a thickness of approximately one micron or other suitable thickness. In other embodiments where visible photon detection is desired, optical isolator 1215 will not be included over intrinsic region 909. Optical isolator 1215 is formed so that respective gaps 1217, 1219 remain between optical isolator 1215 and each of electrodes 1211, 1213. For example, material for isolator 1215 may be deposited so that the material fills the space between electrodes 1211, 1213, and then a patterned etch of the material may be performed to remove material directly adjacent electrodes 1211, 1213 or isolator 1215 could be the same material as the electrodes 1211, 1213 and be patterned concurrently in a single patterning step using conventional lithography and etch steps.

Figure 13:
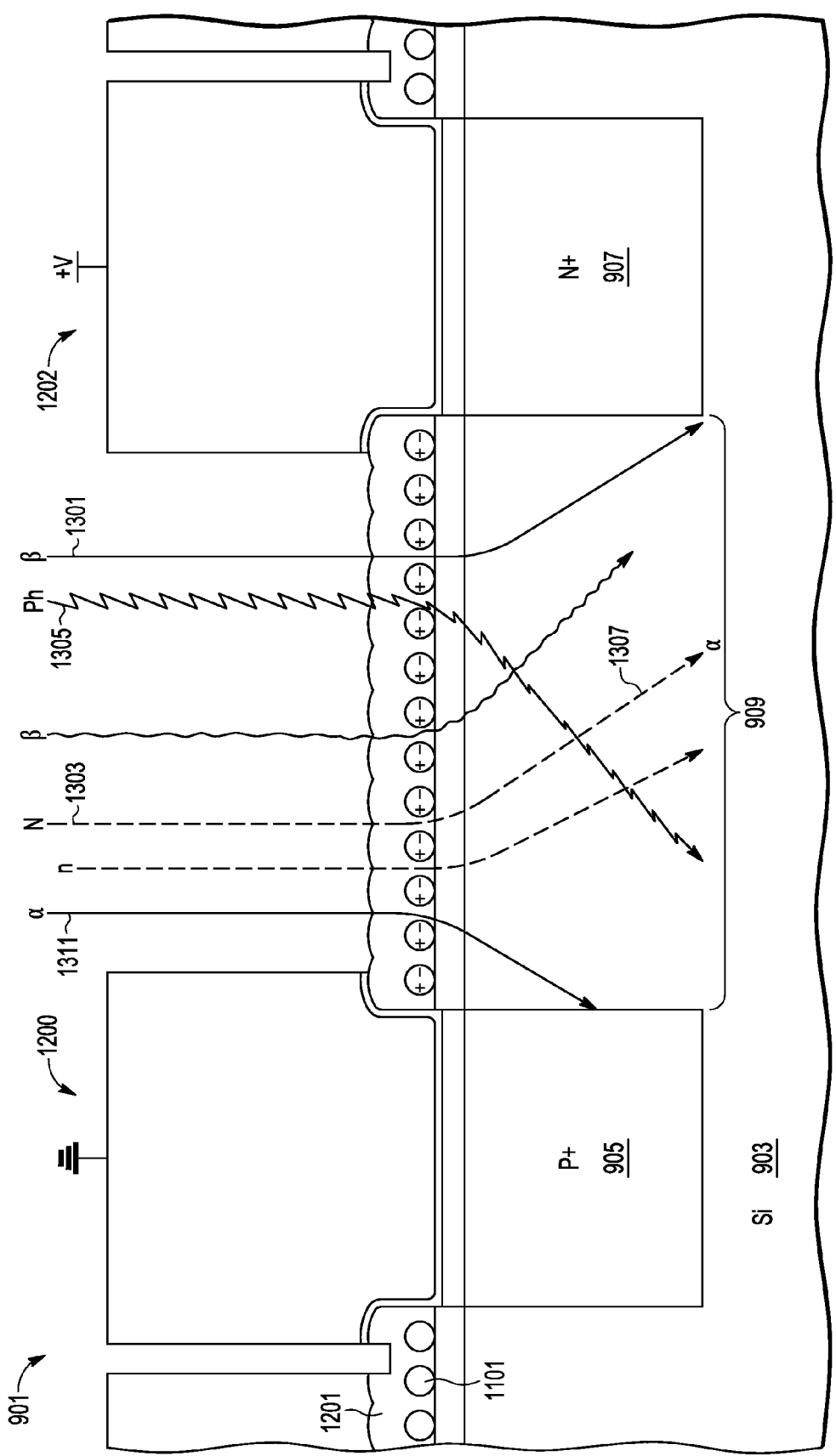
FIG. 13 is a cross-sectional side view of the PIN diode of FIG. 12 showing various types of particles impacting nanoclusters and the intrinsic region, according to an embodiment of the invention.

FIG. 13 is a cross-sectional side view of the PIN diode 901 of FIG. 12 with reverse bias voltages on electrodes 1211, 1213, that is, p-type region 905 is coupled to a first voltage source through electrode 1211 and n-type region 907 is coupled to a second voltage source through electrode 1213. PIN diode 901 can be reverse biased with a voltage at the n-type region 907 of 50 mV, or other suitable voltage while p-type region 905 is coupled to ground, for example. Various types of particles are shown being scattered by nanoclusters 1101 into intrinsic region 909 including beta particle 1301, neutron 1303, alpha particle 1307 that formed when neutron 1303 interacted with the $^{10}$B isotope in nanoclusters 1101, photon 1305, and alpha particle 1311.

Dipole charge of nanoclusters 1101 is indicated by "+" and "−" signs next to each nanocluster 1101 in the reverse biased PIN diode electric field. The dipole charge facilitates deflection of charged species such as alpha particle 1311 and beta particle 1301 into intrinsic region 909, thereby enhancing interaction probability and detection. The magnified electric field at the nanocluster dielectric interface enables enhanced deflection of charged particles improving probability of detection within the underlying PIN diode 901. In particular, charged particles are deflected at the electric dipoles of nanoclusters 1101, supplementing physical scattering effects and enhancing the probability of interaction within intrinsic region 909. The three-dimensional shape of nanoclusters 1101 creates a further physical effect where photon 1305 scatters off adjacent nanoclusters 1101 to enhance absorption of photon 1305 into intrinsic region 909. Further, the $^{10}$B doping of nanoclusters 1101 interacts with neutrons 1303 to generate alpha particle 1307, allowing neutron strikes to be detected with PIN diode 901. Reducing the thickness of insulating layer 911 can further enhance the sensitivity of PIN diode 901 to photons due to reduced light attenuation in insulating layer 911. For example, a PIN diode 901 with an insulating layer 911 having a thickness of 45 Angstroms exhibited greater sensitivity to visible photons 1305 compared to an insulating layer 911 having a thickness of 145 Angstroms.

In some embodiments, intrinsic region 909 may be oriented differently with respect to p-terminal 1200 and n-terminal 1202 than shown in FIGS. 12 and 13. Further, nanoclusters 1101 and insulating layers 1201, 911 may be positioned in any suitable orientation and location in which interaction between particles and intrinsic region 909 can be enhanced by the presence of nanoclusters 1101.

As used herein, the term "radiation" encompasses pure energy (no mass) such as photons as well as energetic species with mass such as subatomic alpha and beta particles.

Figure 14:
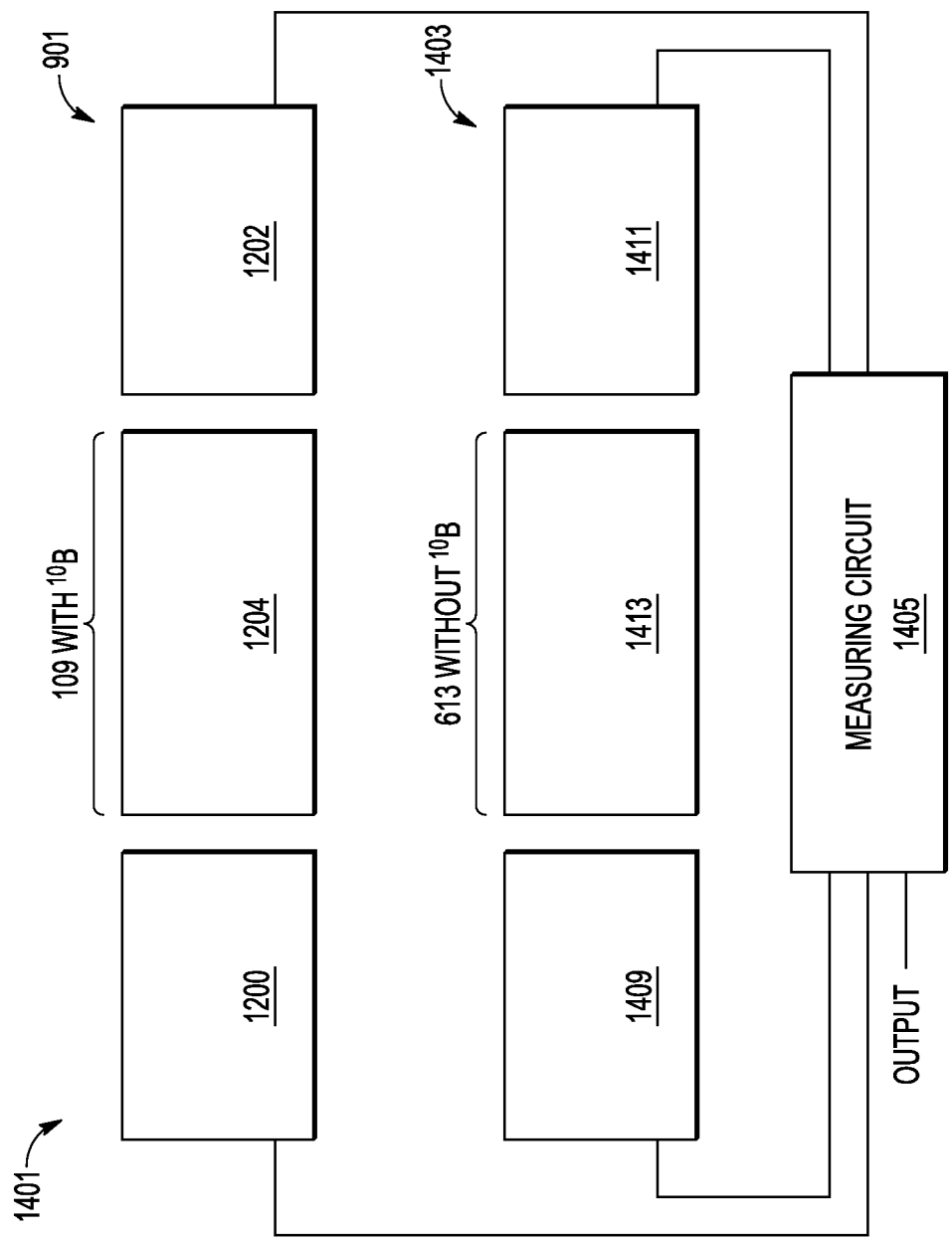
FIG. 14 is block diagram of a sensor system for detecting neutrons, charged particles, and changes in vapor composition in an environment using the PIN diode of FIGS. 1 and/or 13, according to an embodiment of the invention.

Referring to FIGS. 13 and 14, FIG. 14 is a block diagram of an embodiment of a sensor system 1401 for detecting neutrons 1303 that includes both PIN diode 901 of FIG. 13 and PIN diode 1403 coupled to measuring circuit 1405 according to an embodiment of the invention. Sensor system 1401 may also be used to detect changes in vapor composition, such as described for sensor systems 100 and 700 hereinabove. The components of PIN diode 1403 include p-terminal 1409 similar to p-terminal 1200 of PIN diode 901, n-terminal 1411 similar to n-terminal 1202 of PIN diode 901, and detection region 1413 similar to detection region 1204 of PIN diode 901 except detection region 1413 does not include nanoclusters (not shown) in detection region 1413 or any other primary interaction layer doped with $^{10}$B isotope. PIN diodes 901, 1403 are located close enough to one another that a source of neutrons is likely to impact both PIN diodes 901, 1403.

P-terminals 1200, 1409 and n-terminals 1202, 1411 are independently reverse biased to enable measurement in a common sensing environment. Measuring circuit 1405 can supply voltage to bias PIN diodes 901, 1403, and can measure one or more electrical characteristics of PIN diodes 901, 1403, such as voltage, current, resistance, capacitance, among others. Measuring circuit 1405 can include any suitable measuring devices, such as a charge sensitive amplifier, oscilloscope, and/or comparator, etc.

An output of measuring circuit 1405 can indicate the difference in a measured electrical characteristic of PIN diodes 901, 1403. For example, a change in polar vapor composition can be detected by a change in capacitance of pin diode 901 or 1403. As another example, to detect radiation, when neutrons 1303 impact detection region 1204 of PIN diode 901, the interaction of neutrons 1303 with the $^{10}$B isotope in nanoclusters 1101 will generate alpha particles 1307 and create current through PIN diode 901. Since PIN diode 1403 does not include nanoclusters 1101 doped with the $^{10}$B isotope, PIN diode 1403 will not generate alpha particles 1307 from neutrons 1303. The difference in current between PIN diode 901 and PIN diode 1403 indicates a neutron strike since PIN diode 1403 is not capable of generating alpha particles 1307 from neutron 1303 and therefore would be insensitive to it. Note that if both PIN diodes 901, 1403 are struck by alpha particles 1311, alpha particles 1311 will be detected by both PIN diodes 901, 1403 rendering the differential current between the two to be essentially zero.

Figure 15:
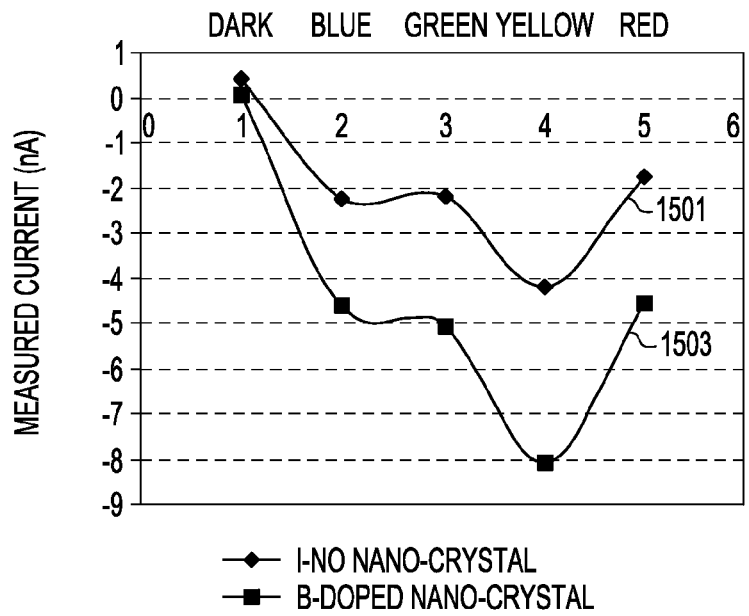
FIG. 15 is a set of graphs showing example test results of the spectral response of the PIN diode of FIG. 13 compared to a conventional PIN diode without nanoclusters.

Referring to FIGS. 13 and 15, FIG. 15 is a set of graphs 1501, 1503 showing test results of the spectral response of PIN diode 901 compared to a conventional PIN diode without nanoclusters 1101 in the visible wavelength. Graph 1501 shows photo electric current measured by PIN diode 1403 and graph 1503 shows current measure in PIN diode 901 in response to photons in the visible wavelength range including blue, green, yellow and red wavelength regions. Table 1 below shows an enhancement ratio of current in nano-Amperes in PIN diode 901 relative to current in PIN diode 1403 at each wavelength region shown by graphs 1501 and 1503:

TABLE 1

| Visible Wavelength Region | Current in PIN Diode 901 (nA) | Current in PIN Diode 1403 (nA) | Enhancement Ratio |
| --- | --- | --- | --- |
| Blue | −4.6 | −2.2 | 2.1 |
| Green | −5 | −2.1 | 2.4 |
| Yellow | −8.1 | −4.1 | 2.0 |
| Red | −4.6 | −1.8 | 2.6 |

As the results of graphs 1501 and 1503 show, PIN diode 901 is more sensitive to photon detection than PIN diode 1403. The difference in sensitivity peaks in the yellow wavelength region with a difference of 4 nA between current in PIN diode 901 and PIN diode 1403, but is still significant in the blue, green and red wavelength regions. The enhanced photoelectric response of PIN diode 901 compared to PIN diode 1403 is due to scattering of photons by nanoclusters 1101, which effectively increases interaction probability and hence absorption in intrinsic region 909.

A measurement system for detecting alpha particles can include output from PIN diode 901 being provided to a charge sensitive amplifier module such as the Cremat CR-Z-110 by Cremat Corporation in West Newton, Mass. In one test, the amplified output of the amplifier was input to an oscilloscope. It was demonstrated that an alpha strike from a thorium source with a fluence of 70/cm$^2$/sec and peak energy of 4 MeV could be detected by PIN diode 901 at a signal to noise ratio of 5:1.

Figure 16:
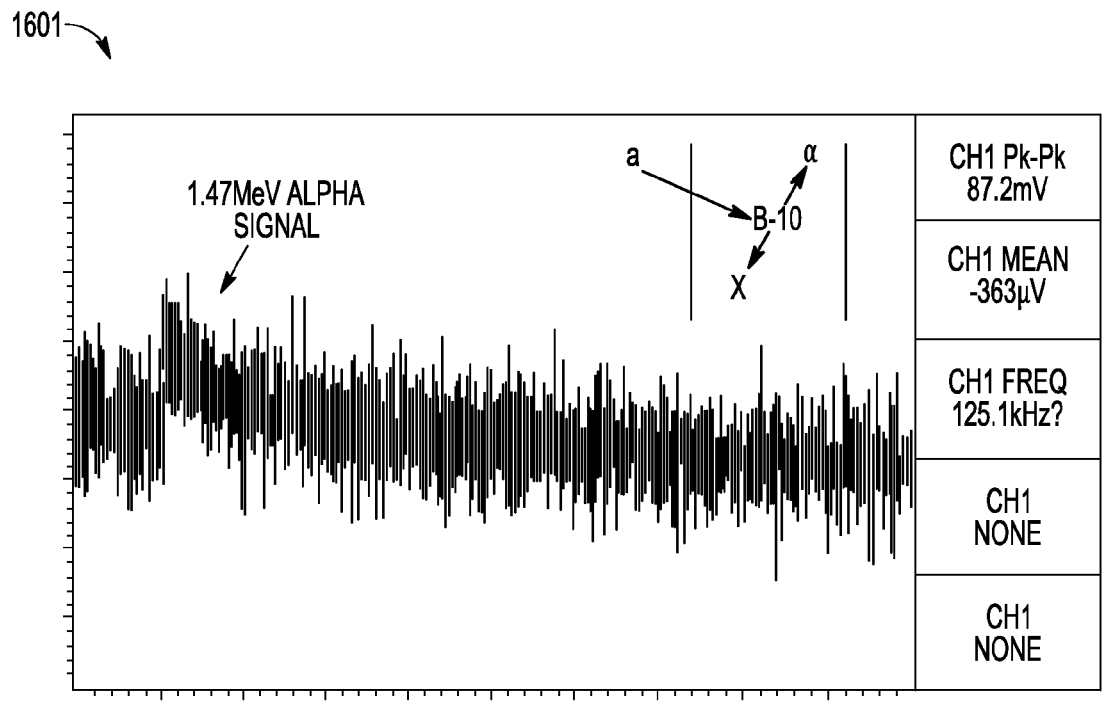
FIG. 16 is a graph of an example of an amplified output of PIN diode of FIG. 13 upon a 10 meV cold neutron strike.

FIG. 16 is a graph 1601 of an example of an amplified output of PIN diode 901 of FIG. 13 upon a 10 meV cold neutron strike. Amplification of the signal was performed using a Cremat CR-Z-110 charge sensitive amplifier by Cremat Corporation in West Newton, Mass. The signal elevation shown is from a secondary alpha particle generated upon interaction of the 10 meV Neutrons with $^{10}B$ isotope in nanocluster 1101. This data proves the concept of using $^{10}B$ isotope doping of nanoclusters for detecting thermal neutrons.

Figure 17:
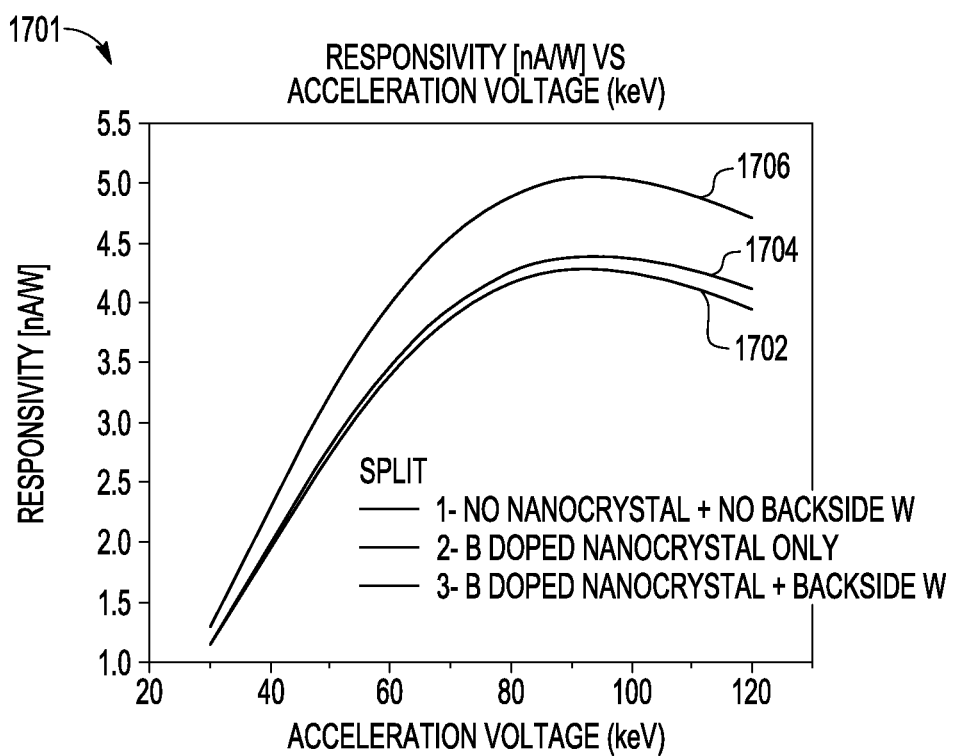
FIG. 17 shows an example of the output of three variants of PIN diode of FIG. 13 exposed to X-radiation.

In some embodiments, a high atomic number material such as Tungsten can be coated on the backside of PIN diode 901 to enhance radiation detection sensitivity via Bremsstrahlung and/or characteristic back-radiation effects. FIG. 17 of graph 1701 shows response of three types of PIN diode 901 variants, 1702, 1704 and 1706 to X-radiation. Trace 1702 is the responsivity of a baseline device 901 with no nanoclusters or backside Tungsten. Trace 1704 is the responsivity of device 901 variant with nanoclusters but no backside Tungsten while trace 1706 corresponds to a device 901 variant with both nanoclusters and backside Tungsten being present. The variant with both nanoclusters 1101 as well as the backside Tungsten coating as shown in trace 1706 exhibited the highest responsivity of the three variants. The data in graph 1701 proves the sensitivity enhancement benefits of the nanoclusters as well as the backside Tungsten concepts.

By now, it should be appreciated that a radiation sensing device has been provided that includes a reverse biased PIN diode 901 with $^{10}B$ nanoclusters 1101 connected in parallel with the intrinsic region 909, and a thin insulative layer 911 between the nanoclusters 1101 and intrinsic region 909. An embodiment in which a high atomic number film on the backside of substrate 102 to further enhance the sensitivity of device 901 has also been demonstrated. PIN diode 901 thereby is designed to synergistically enhance the capability and versatility of conventional PIN diodes enabling higher sensitivity and broader range of photo and ionization detection at reduced cost.

In some embodiments, a diode includes a first electrode (106) to which an electric field is applied; a second electrode (108) to which the electric field is applied; and a vapor gap region (120) between the first electrode and the second electrode. A total capacitance (Ceq) measured between the first electrode and the second electrode varies based on presence of a polar vapor species on at least a portion of an electrode surface of at least one of the first electrode and the second electrode.

In another aspect, molecules of the polar vapor species form an electric double layer (116 or 118) at the portion of the electrode surface upon application of a low frequency alternating voltage signal (112) between the first and second electrodes. Capacitance (CEN, CEP) due to the electric double layer increases proportionally with an increase in concentration of the molecules of the polar vapor species present on the portion of the electrode surface. The total capacitance includes the capacitance due to the electric double layer.

In another aspect, the low frequency alternating voltage signal can have a frequency of less than 500 Hz.

In another aspect, the first electrode can comprise a first plurality of fingers (204 of FIG. 2), the second electrode comprises a second plurality of fingers (206 of FIG. 2), and the first and second plurality of fingers form an interdigitated structure.

In another aspect, a spacing (S of FIG. 2) measured between a finger of the first plurality of fingers and an adjacent finger of the second plurality of fingers can be less than or equal to 4 microns.

In another aspect, the first and second electrodes can comprise a passive conductive metal, and the passive conductive metal can comprise one of a group including aluminum and titanium nitride.

In another aspect, the diode can further comprise a first semiconductor region (103) of a first conductivity type in ohmic contact with the first electrode, and a second semiconductor region (104) of a second conductivity type in ohmic contact with the second electrode. The second conductivity type is opposite the first conductivity type. An intrinsic semiconductor region can be included between the first and second semiconductor regions, wherein the vapor gap region is above the intrinsic semiconductor region.

In another aspect, the diode can further comprise at least one or more of: a layer of nanoclusters (1101) located over the intrinsic semiconductor region, and a layer of non-conductive material (1201) located over the intrinsic semiconductor region.

In other embodiments, a device can comprise a diode that includes a first electrode (106) to which an electric field is applied, a second electrode (108) to which the electric field is applied, and a vapor gap region (120) between the first electrode and the second electrode. A total capacitance (Ceq) measured between the first electrode and the second electrode varies based on presence of a first polar vapor species on at least a portion of an electrode surface of at least one of the first electrode and the second electrode. A measuring circuit (114) includes a first terminal electrically coupled to the first electrode and a second terminal electrically coupled to the second electrode. The measuring circuit can be configured to provide a reading of the total capacitance measured between the first electrode and the second electrode.

In another aspect, molecules of the first polar vapor species can form an electric double layer (116 or 118) at the portion of the electrode surface upon application of a low frequency alternating voltage signal (112) between the first and second electrodes. A capacitance (CEN, CEP) due to the electric double layer increases proportionally with an increase in concentration of the molecules of the first polar vapor species present on the portion of the electrode surface, and the total capacitance includes the capacitance due to the electric double layer.

In another aspect, the device can further comprise a power source (112) having a first terminal electrically coupled to the first electrode and a second terminal electrically coupled to the second electrode. The power source can be configured to apply the low frequency alternating voltage signal to the first and second electrodes.

In another aspect, the device can further comprise a selectively reactive source (704) configured to selectively react with the first polar vapor species (e.g., acetone) present within the vapor gap region and in vicinity of the first and second electrodes to produce one or more component nonpolar vapor species (e.g., $CO_2$, $O_2$), wherein a second polar vapor species (e.g., water vapor) is also present within the vapor gap region and in vicinity of the first and second electrodes.

In another aspect, the selectively reactive source comprises at least one or more of: a light source (704) configured to expose the first polar vapor species to light of a suitable wavelength capable of selectively inducing photochemical decomposition of the first polar vapor species, and a chemical source configured to expose the first polar vapor species to a chemical compound.

In another aspect, the device can further comprise a logic circuit configured to initiate the measurement circuit to provide a first reading of the total capacitance between the first and second electrodes, activate the selectively reactive source to selectively react with the first polar vapor species for a period of time subsequent to initiation of the first reading of the total capacitance, and initiate the measurement circuit to provide a second reading of the total capacitance between the first and second electrodes subsequent to activation of the selectively reactive source.

In still other embodiments, a method can comprise applying an electric field to a first electrode (106) and a second electrode (108) of a diode, wherein the first electrode and the second electrode are separated by a vapor gap region (120) of the diode, and measuring a total capacitance between the first electrode and the second electrode, wherein the total capacitance varies based on presence of a first polar vapor species on at least a portion of an electrode surface of at least one of the first electrode and the second electrode.

In another aspect, the method can further comprise introducing a vapor sample to the vapor gap region, wherein the vapor sample comprises the first polar vapor species.

In another aspect, the method can further comprise measuring a first reading of the total capacitance between the first and second electrodes, wherein the vapor sample further comprises a second polar vapor species (e.g., water vapor); exposing the vapor sample present within the vapor gap region and in vicinity of the first and second electrodes to a selectively reactive source that selectively reacts with the first polar vapor species (e.g., acetone) to produce one or more component non-polar vapor species (e.g., $CO_2$, $O_2$), wherein the exposing is performed for a period of time subsequent to the measuring the first reading; and measuring a second reading of the total capacitance between the first and second electrodes, wherein the measuring of the second reading is performed subsequent to the exposing the vapor sample.

In another aspect, the selectively reactive source (704) comprises at least one or more of: a light source configured to expose the vapor sample to light of a suitable wavelength capable of inducing photochemical decomposition of the first polar vapor species, and a chemical source configured to expose the vapor sample to a chemical compound.

In another aspect, a difference between the first reading and the second reading correlates to a particular concentration of the first polar vapor species (e.g., acetone) present on the portion of the electrode surface at a time of the first reading.

In another aspect, the first polar vapor species comprises one of a group including ketones, water vapor, and alcohol.

The terms "top," "bottom," "over," "under," "overlying," "underlying," and the like in the description and in the claims, if any, are used for descriptive purposes and may, but do not necessarily, describe permanent relative positions. It is understood that the terms so used may be interchangeable under appropriate circumstances such that the embodiments of the invention described herein are, for example, capable of operation in other orientations than those illustrated or otherwise described herein.

The terms "a" or "an," as used herein, are defined as one or more than one. Also, the use of introductory phrases such as "at least one," "at least two," and "one or more" in the claims should not be construed to imply that the introduction of another claim element by the indefinite articles "a" or "an" limits any particular claim containing such introduced claim element to devices, etc., containing only one such element, even when the same claim includes the introductory phrases "one or more" or "at least one" and indefinite articles such as "a" or "an." The same applies to the use of definite articles.

Although the invention is described herein with reference to specific embodiments, various modifications and changes can be made without departing from the scope of the present invention as set forth in the claims below. Accordingly, the specification and figures are to be regarded in an illustrative rather than a restrictive sense, and all such modifications are intended to be included within the scope of the present invention. Any benefits, advantages, or solutions to problems that are described herein with regard to specific embodiments are not intended to be construed as a critical, required or essential feature or element of any or all of the claims.

What is claimed:
1. A diode comprising:
a first electrode to which an electric field is applied;
a second electrode to which the electric field is applied;
a vapor gap region between the first electrode and the second electrode, wherein
   a total capacitance measured between the first electrode and the second electrode varies based on presence of a polar vapor species on at least a portion of an electrode surface of at least one of the first electrode and the second electrode;
a first semiconductor region of a first conductivity type in ohmic contact with the first electrode;
a second semiconductor region of a second conductivity type in ohmic contact with the second electrode, wherein
   the second conductivity type is opposite the first conductivity type; and
an intrinsic semiconductor region between the first and second semiconductor regions, wherein the vapor gap region is above the intrinsic semiconductor region.

2. The diode of claim 1, wherein
molecules of the polar vapor species form an electric double layer at the portion of the electrode surface upon application of a low frequency alternating voltage signal between the first and second electrodes,
a capacitance due to the electric double layer increases proportionally with an increase in concentration of the molecules of the polar vapor species present on the portion of the electrode surface, and
the total capacitance includes the capacitance due to the electric double layer.

3. The diode of claim 2, wherein
the low frequency alternating voltage signal has a frequency of less than 500 Hz.

4. The diode of claim 1, wherein
the first electrode comprises a first plurality of fingers,
the second electrode comprises a second plurality of fingers, and
the first and second plurality of fingers form an interdigitated structure.

5. The diode of claim 4, wherein
a spacing measured between a finger of the first plurality of fingers and an adjacent finger of the second plurality of fingers is less than 4 microns.

6. The diode of claim 1, wherein
the first and second electrodes comprise a passive conductive metal, and the passive conductive metal comprises one of a group including aluminum and titanium nitride.

7. The diode of claim 1, further comprising at least one or more of:
   a layer of nanoclusters located over the intrinsic semiconductor region, and
   a layer of non-conductive material located over the intrinsic semiconductor region.

8. A device comprising:
   a diode, the diode comprising:
      a first electrode to which an electric field is applied,
      a second electrode to which the electric field is applied, and
      a vapor gap region between the first electrode and the second electrode, wherein a total capacitance measured between the first electrode and the second electrode varies based on presence of a first polar vapor species on at least a portion of an electrode surface of at least one of the first electrode and the second electrode;
   a first semiconductor region of a first conductivity type in ohmic contact with the first electrode;
   a second semiconductor region of a second conductivity type in ohmic contact with the second electrode, wherein the second conductivity type is opposite the first conductivity type;
   an intrinsic semiconductor region between the first and second semiconductor regions, wherein the vapor gap region is above the intrinsic semiconductor region; and
   a measuring circuit having a first terminal electrically coupled to the first electrode and a second terminal electrically coupled to the second electrode, wherein the measuring circuit is configured to provide a reading of the total capacitance measured between the first electrode and the second electrode.

9. The device of claim 8, wherein
   molecules of the first polar vapor species form an electric double layer at the portion of the electrode surface upon application of a low frequency alternating voltage signal between the first and second electrodes,
   a capacitance due to the electric double layer increases proportionally with an increase in concentration of the molecules of the first polar vapor species present on the portion of the electrode surface, and
   the total capacitance includes the capacitance due to the electric double layer.

10. The device of claim 9, further comprising a power source having a first terminal electrically coupled to the first electrode and a second terminal electrically coupled to the second electrode, wherein the power source is configured to apply the low frequency alternating voltage signal to the first and second electrodes.

11. The device of claim 8, further comprising:
   a selectively reactive source configured to selectively react with the first polar vapor species present within the vapor gap region and in vicinity of the first and second electrodes to produce one or more component non-polar vapor species, wherein a second polar vapor species is also present within the vapor gap region and in vicinity of the first and second electrodes.

12. The device of claim 11, wherein the selectively reactive source comprises at least one or more of:
   a light source configured to expose the first polar vapor species to light of a suitable wavelength capable of selectively inducing photochemical decomposition of the first polar vapor species, and
   a chemical source configured to expose the first polar vapor species to a chemical compound.

13. The device of claim 11, further comprising:
   a logic circuit configured to
      initiate the measurement circuit to provide a first reading of the total capacitance between the first and second electrodes,
      activate the selectively reactive source to selectively react with the first polar vapor species for a period of time subsequent to initiation of the first reading of the total capacitance, and
      initiate the measurement circuit to provide a second reading of the total capacitance between the first and second electrodes subsequent to activation of the selectively reactive source.

\* \* \* \* \*